US009310359B2

(12) United States Patent
Jensen et al.

(10) Patent No.: US 9,310,359 B2
(45) Date of Patent: Apr. 12, 2016

(54) ANALYTE QUANTIFICATION USING FLOW INDUCED DISPERSION ANALYSIS

(75) Inventors: Henrik Jensen, Roskilde (DK); Jesper Ostergaard, Farum (DK)

(73) Assignee: FIDA-TECH APS, Roskilde (DK)

( * ) Notice: Subject to any disclaimer, the term of this patent is extended or adjusted under 35 U.S.C. 154(b) by 0 days.

(21) Appl. No.: 13/582,220

(22) PCT Filed: Feb. 25, 2011

(86) PCT No.: PCT/EP2011/052844
§ 371 (c)(1),
(2), (4) Date: Nov. 13, 2012

(87) PCT Pub. No.: WO2011/107406
PCT Pub. Date: Sep. 9, 2011

(65) Prior Publication Data
US 2013/0059313 A1    Mar. 7, 2013

Related U.S. Application Data

(60) Provisional application No. 61/309,384, filed on Mar. 1, 2010.

(51) Int. Cl.
*G01N 33/50* (2006.01)
*G01N 33/536* (2006.01)
*G06F 19/26* (2011.01)
*G06G 7/58* (2006.01)
*G01N 21/17* (2006.01)

(52) U.S. Cl.
CPC .............. *G01N 33/536* (2013.01); *G06F 19/26* (2013.01); *G01N 21/17* (2013.01)

(58) Field of Classification Search
CPC ......... G06F 19/26; G01N 21/17; G01N 33/50
See application file for complete search history.

(56) References Cited

U.S. PATENT DOCUMENTS

2007/0261479 A1    11/2007    Spaid et al.

FOREIGN PATENT DOCUMENTS

WO    2005/113148    12/2005

OTHER PUBLICATIONS

Attal et al. "Determination of the Concentration of Single-Walled Carbon Nanotubes in Aqueous Dispersions Using UV-Visible Absorption Spectroscopy" Anal. Chem, 2006, vol. 27, pp. 8098-8104.*
Cottet, H., et al., Taylor Dispersion Analysis of Mixtures, Anal. Chem. 2007; 79: 9066-9073.
Taylor, G., Dispersion of Soluble Matter in Solvent Flowing Slowly Through a Tube, Proceedings of the Royal Society of London, Series A, Mathematical and Physical Sciences, 1953; 219 (1137): 186-203.
Aris, R., On the Dispersion of a Solute in a Fluid Flowing Through a Tube, Proceedings of the Royal Society of London, Series A, Mathematical and Physical Sciences, vol. 235, No. 1200 (Apr. 10, 1956), pp. 67-77.
Taylor, G., Conditions under which Dispersion of a Solute in a Stream of Solvent can be Used to Measure Molecular Diffusion, Proceedings of the Royal Society of London, Series A, Mathematical and Physical Sciences, 1954; (1163): 473-477.
Lucas, L., et al., Epitope Mapping and Competitive Binding of HSA Drug Site II Ligands by NMR Diffusion Measurements, American Chemical Society, 2004; 126: 14258-14266.
Rekharsky, M. V., et al., Complexation Thermodynamics of Cyclodextrins, American Chemical Society, Rev. 1998; 98: 1875-1917.
Bourne, J. R., et al., Measurement of the Diffusivity of 1-Naphthol in Water with a Rotating Disc, Chemical Engineering Communications, 1985; 36: 67-71.
Zhang, H., et al., Diffusion of an Ionic Drug in Micellar Aqueous Solutions, Langmuir, 2009; 25: 3425-3434.
Jensen, H., et al., Flow Induced Dispersion Analysis Quantifies Noncovalent Interactions in Nanoliter Samples, Journal of American Chemical Society, 2010; 132: 4070-4071.
Ferguson, P.D. et al, Journal of Chromatography A, 1997; 768: 29-38.
Drews, J., Drug Discovery: A Historical Perspective, Science, 2000; 287: 1960-4.
Weigl, B. H., et al., Lab-on-a-chip for drug development, Advanced Drug Delivery Reviews, 2000; 55: 349-77.
Bello, M. S., et al., Use of Taylor-Avis Dispersion for Measurement of a Solute Diffusion Coefficient in Thin Capillaries, Science 1994; 266 (Nov. 4): 773-776.
Cottet, H., et al., Determination of Dendrigraft Poly-L-Lysine Diffusion Coefficients by Taylor Dispersion Analysis, Biomacromolecules, 2007; 8: 3235-3243.
Le Saux, T., et al., Size-Based Characterization by the Coupling of Capillary Electrophoresis to Taylor Dispersion Analysis, Analytical Chemistry, 2008; 80 (5):1829-1832.
D'Orlye, F., et al., Determination of nanoparticle diffusion coefficients by Taylor dispersion analysis using a capillary electrophoresis instrument, Journal of Chromatography A, 2008; 1204: 226-232.
Ostergaard, J., et al., Simultaneous Evaluation of Ligand Binding Properties and Protein Size by Electrophoresis and Taylor Dispersion in Capillaries, Anal. Chem., 2009; 81: 8644-8648.
Sharma, U., et al., Diffusivity of Solutes Measured in Glass Capillaries Using Taylor's Analysis of Dispersion and a Commercial CE Instrument, Anal. Chem., 2005; 77: 806-813.
Burkey, T. J., Simple Method for Quantifying the Distribution of Organic Substrates between the Micellar and Aqueous Phases of Sodium Dodecyl Sulfate Solution, American Chemical Society, 1984;106: 1983-198.

(Continued)

*Primary Examiner* — Eric S Dejong
(74) *Attorney, Agent, or Firm* — Polsinelli PC; Ron Galant (57) ABSTRACT

A method for quantitative characterization of non-covalent interactions and analyte quantification in nanoliter samples is described. The procedure is based on Flow Induced Dispersion Analysis (FIDA), of which the only system requirements is a narrow tube, capillary or channel equipped with a detector. The technique can be implemented using standard equipment such as High Performance Liquid Chromatography (HPLC), Flow Injection Analysis (FIA) or Capillary Electrophoresis (CE).

18 Claims, 8 Drawing Sheets

(56) References Cited

OTHER PUBLICATIONS

Montanari, M. L. C., et al., Determination of Log P app for Drug Transfer to Microbial Cellular Systems via the Taylor-Aris Modified Diffusion Technique, Quant. Struct.-Act. Rel. 1998; 17: 102-108.

Clark, S. M., et al., Diffusion Measurements by Electrospray Mass Spectrometry for Studying Solution-Phase Noncovalent Interactions, American Society for Mass Spectrometry, 2003; 14: 430-441.

* cited by examiner

Bromocresol green - Human serum albumin (HSA)

Determination of HSA in urine (UV - detection)

Figure 10

ANALYTE QUANTIFICATION USING FLOW INDUCED DISPERSION ANALYSIS

CROSS-REFERENCE TO RELATED APPLICATIONS

This is the national stage of International Application No. PCT/EP2011/052844, filed on Feb. 25, 2011, which claims the benefit of U.S. Provisional Patent Application No. 61/309,384, filed on Mar. 1, 2010, the contents of all of which are hereby incorporated herein by reference.

Non-covalent interactions play a key role in many biochemical processes related to for example drug targets or protein-protein interactions (1). In combinatorial chemistry and in drug development a large number of non-covalent interactions need to be addressed in a limited time frame.

Often a very small sample amount is available for study which prevents a comprehensive characterization using existing methods. Furthermore, it is complicated from a technological point of view to integrate standard procedures for addressing non-covalent interactions with binding target isolation and/or synthesis of chemical entities (1,2).

US 2007/0261479 discloses methods and systems for monitoring molecular interactions using the phenomenon of Taylor-Aris dispersion present in fluid flow in microfluidic systems for screening test compounds in biochemical systems.

SUMMARY OF THE INVENTION

The present invention concerns the use of Flow Induced Dispersion Analysis (FIDA) for quantification of analytes such as e.g. antigens, toxins, nucleotides (DNA, RNA), etc. For pressure driven flows of single substances FIDA is similar to Taylor Dispersions observed previously for pressure driven flows in tubes or thin capillaries. Compared to existing methods the new approach is fast (seconds/minutes compared to hours) cheap (low sample volume (nL) requirements) and easy to implement (requires only a thin capillary tube and a detector).

Possible application areas includes: biomarker quantification, point-of-care diagnostics and as a general approach for analyte quantification in flow based analytical equipment for laboratory analysis. The same procedure may be used for several analytes in an integrated system.

Large molecules diffuse slowly and small molecules diffuse comparatively faster. When a molecule interacts with a ligand its apparent diffusivity becomes that of the complex. The apparent diffusivity of a ligand is thus dependent on the fractions of free and complexed analyte which in turn is given by the non-covalent analyte-ligand equilibrium binding constant. The underlying idea of the present invention is that the apparent dispersion of a ligand in a flow system is characterized by the apparent diffusivity of the ligand. It is well-known that peak dispersion may be used to asses the diffusivity of small molecules, macromolecules and particles (3-8). However, only a few studies have reported dispersion in systems with several components (9-12). By measuring the diffusivity of an indicator molecule (the affinity probe or ligand) in the presence and absence of an interacting analyte it is thus possible to obtain information of the concentration of the interacting analyte.

In the present invention we demonstrate that a simple series of experiments involving sample introduction, pressure driven flow and detection in a thin coated silica capillary can be used to quantify non-covalent equilibrium binding constants as well as the concentration of one or more analytes in a sample.

Molecular diagnostics usually involves a non-covalent interaction between a specific biomarker (often endogenous macromolecules, vira or bacteria) and an antibody or a DNA/RNA probe. From such a specific non-covalent interaction, the concentration of biomarkers can be obtained using FIDA; the technology is therefore well suited for fast quantitative diagnosis, including point-of-care diagnostics.

FIDA for quantification of analyte concentrations offers a new approach for performing quantitative analyses. The main advantages of the present technique are analysis speed, simplicity in relation to assay development and low cost.

According to a first aspect of the present invention, the method for measuring the concentration of an analyte in a sample comprising the following steps:
1) selecting a ligand as an affinity probe for the analyte to be measured,
2) determine in a flow based instrumentation the variance for said ligand,
3) determine the variance in the same instrumentation for the same concentration of said ligand in the presence of different (known) concentrations of the analyte,
4) relate the concentrations of analyte to the variances determined in step 3,
5) adding a known amount of ligand to a sample comprising an unknown concentration of analyte,
6) determine the variance for the ligand in the sample introduced/added in step 5, and
7) determine the concentration of the analyte in said sample by using the relationship established in step 4 and the variance determined in step 6.

A second aspect of the present invention concerns a method comprising the following steps:
1) selecting a ligand as an affinity probe for the analyte to be measured,
2) determine in a flow based instrumentation, such as e.g. an agilent CE system, the variance ($\sigma^2$) for said ligand, obtained from a Gaussian fit to the peak corresponding to the ligand,
3) repeating step 2 with said ligand and different known concentrations of the analyte,
4) plotting $\sigma^2$ or $\sigma^2/tr$ against the analyte concentration,
5) determine the variance ($\sigma^2$) for the ligand in a sample comprising the analyte, and
6) determine the concentration of the analyte in said sample by using the plot from step 4.

In other aspects of the present invention, the method concerns flow based instrumentation including instruments dedicated to an agilent CE, HPLC or FIA system and methods wherein the ligand comprises a detectable label and methods wherein the sample is selected from any bodily fluid or food sample.

In further aspects, the invention concerns kits for performing the above described method and kits for performing steps parts of the methods, for example where standard curves are already established for use in the kit and kits for use in measuring amounts of analyte bodily fluids or food samples.

In yet another aspect of the present invention, more than one analyte can be measured in the same method and using the same kit.

BRIEF DESCRIPTION OF THE FIGURES

FIG. 5. Binding isotherm based on peak variances, $\sigma^2$. The UV signal was detected at 495 nm and preconditioning was as described in FIG. 2. The analyte was anti-BSA (monoclonal anti-bovine serum albumin produced in mouse, Sigma B2901) and the ligand was Albumin fluorescein isothiocyanate (Sigma A9771). This figure is based on the data obtained in example 3

DETAILED DESCRIPTION OF THE INVENTION

The present invention concerns a new approach for quantitative characterization of non-covalent interactions and analyte quantification in nanoliter samples. As the procedure is based on Flow Induced Dispersion Analysis (FIDA), the only system requirements is a narrow tube, capillary or channel equipped with a detector having a linear response. The technique may therefore be implemented using standard equipment for e.g. High Performance Liquid Chromatography (HPLC), Flow Injection Analysis (FIA) or Capillary Electrophoresis (CE) (disclosed in US 2007/0261479, which is hereby incorporated by reference).

In the illustrative examples of the present invention UV and fluorescence detection is used, but other detectors based on e.g. electrochemistry or mass spectrometry should also be applicable. The detectable signal can be generated by the molecules as internal labels or by the use of external labels attached to the molecules (the ligand).

The selected chemical system illustrating the present invention is composed of β-cyclodextrin (βCD) as the analyte and α-naphthol or naproxen as ligands (affinity probes). In general the equilibrium corresponding to the formation of a 1 to 1 complex can be written as:

$$A + L \leftrightarrow AL \qquad (1)$$

where A is the analyte, L the ligand and AL the complex.

Figure 1:
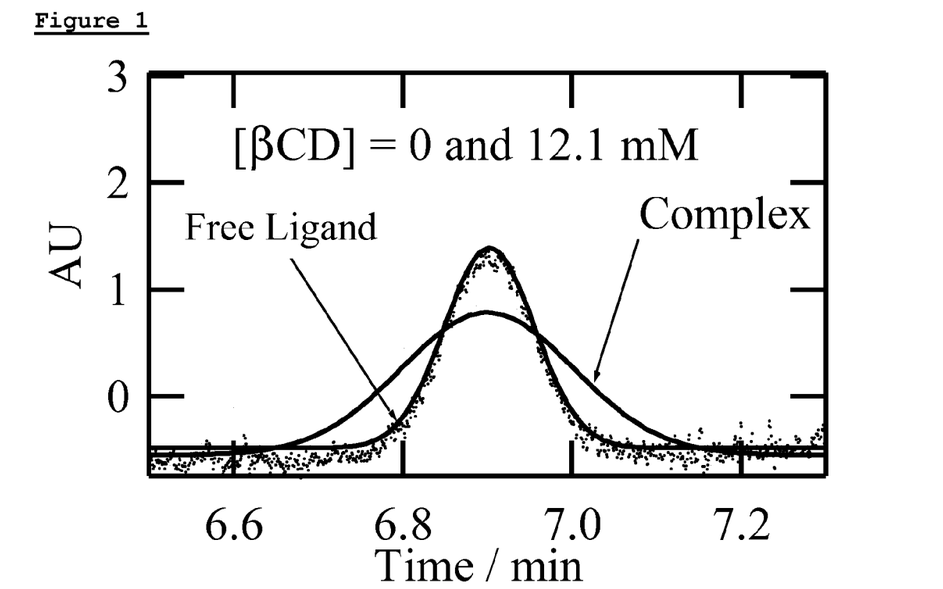
FIG. 1. UV trace at 230 nm and 25° C. of α-naphthol (50 µM) in the presence and absence of βCD in a fused silica capillary (i.d.: 50 μm, total length 48.5 cm, length to detector 40.5 cm). The eluent was 67 mM sodium phosphate buffer (pH 7.4) with or without βCD.

In FIG. 1 is shown the peaks corresponding to α-naphthol (ligand) in the absence and presence of βCD in the run buffer solution, respectively. The sample volume introduced into the capillary in these experiments corresponds to 9 nL. It is immediately apparent that in the presence of βCD the peaks are wider. The peak shape may be fitted to a Gaussian peak shape (described in the examples); in this way the temporal peak variance $\sigma^2$ can be estimated. The variance may be established in any other way known to the skilled person.

According to Taylor-Aris theory the temporal peak variance is related to ligand (affinity probe) diffusivity (13,14). Under optimal conditions for a pressure driven flow in a cylindrical capillary the peak variance is inversely proportional to the diffusion coefficient, D, according to (15):

$$D = \frac{R_c^2}{24\sigma^2} t_R \qquad (2)$$

where Rc is the radius of the capillary tube, and tR is the peak appearance time. In the presence of the analyte βCD, the observed variance can be attributed to α-naphthol and the complex between α-naphthol and βCD. We shall assume that the observed variance is a weighted average depending on the fraction of free α-naphthol, x. This assumption is valid when the complexation kinetics is fast compared to the timescale of the experiment (16).

As the complex and free ligand are both non-retained they have identical tR values. We may thus obtain:

$$\frac{t_R}{\sigma^2} = \frac{t_R}{\sigma_A^2} \cdot x + \frac{t_R}{\sigma_{AL}^2} \cdot (1-x) \qquad (3)$$

where $\sigma_A^2$ is the observed variance obtained from a Gaussian fit in the absence of an interacting analyte and $\sigma_{AL}^2$ is the variance corresponding to the complex AL. Alternatively, eq (2) may be written in terms of diffusion coefficients. However, the present parameter choice is convenient as it is systems independent (i.e. precise knowledge of channel size and radius is not required) as long as the Taylor conditions are satisfied. Corrections due to sample injection and detector variances may be introduced, but as they are small and constant under the present conditions they are neglected.

The fraction of free ligand, x, can also be expressed according to the equilibrium binding constant, K:

$$x = \frac{1}{1+K[L]} \quad (4)$$

where [L] is the concentration of free analyte. Under the present conditions βCD is in a large excess and [L] can therefore be approximated by the total ligand concentration.

Combination of equation 3 and 4 gives the binding isotherm:

$$\frac{t_R}{\sigma^2} = \frac{\frac{t_R}{\sigma_A^2} + \frac{t_R}{\sigma_{AL}^2}K[L]}{1+K[L]} \quad (5)$$

Eq 5 can be extended to higher order complexes if necessary.

Figure 2:
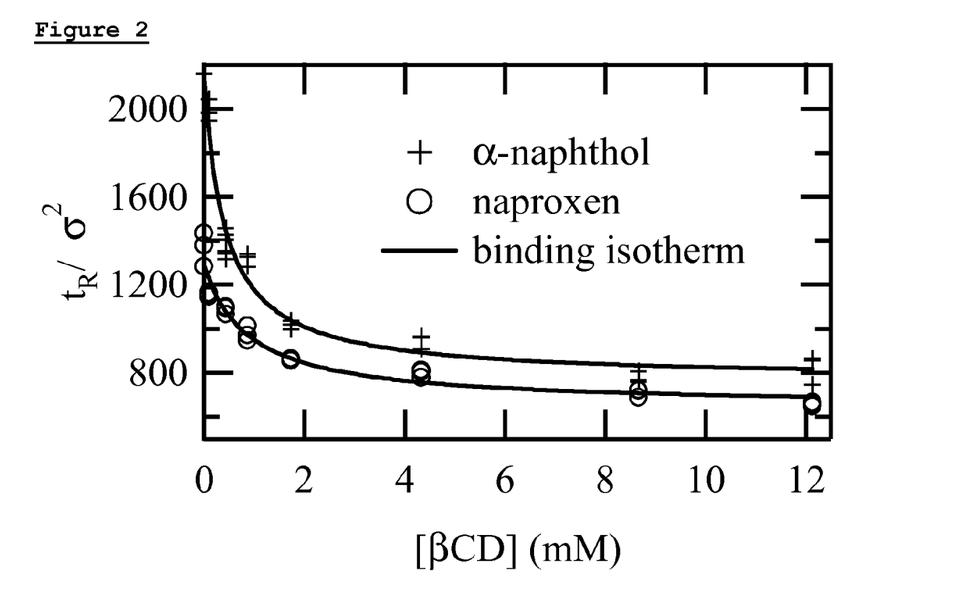
FIG. 2. Data corresponding to α-naphthol (+) and naproxen (o) obtained using a fused silica capillary (id: 50 μm, total length 48.5 cm, length to detector 40.5 cm) at 25° C. The eluent was 67 mM sodium phosphate buffer pH 7.4 with different amounts of βCD.

In a series of experiments the concentration of βCD in the background electrolyte was varied and the peak variances determined. In FIG. 2 is shown $t_R/\sigma^2$ as a function of [βCD].

In FIG. 2 the experimental data have been fitted to the binding isotherm (K and $\sigma_{AL}^2/t_R$ are the fitting parameters). The experimental points are found to be well described by the model and the estimated binding constants are in good agreement with literature data considering that other methods and different conditions were used (table 1). In table 1, the diffusion coefficients of the analytes and complexes calculated using eq 2 and assuming a capillary radius of 25 µm are also listed.

TABLE 1

Equilibrium binding constants (K) and diffusion coefficients of free analytes (DA) and complexes (DAL), respectively, obtained in 67 mM phosphate buffer (pH 7.4) at 25° C.

| Compound | $K^a$ (M$^{-1}$) | $D_A^b$ (cm$^2$ s$^{-1}$) | $D_{AL}^c$ (cm$^2$ s$^{-1}$) |
|---|---|---|---|
| α-Naphthol | 2400 (±240) | 9.3 · 10$^{-6}$ | 3.3 · 10$^{-6}$ |
| | 1250$^d$ | 9.2 · 10$^{-6e}$ | |
| Naproxen | 1050 (±185) | 5.6 · 10$^{-6}$ | 2.8 · 10$^{-6}$ |
| | 650 (±28)$^f$ | 5.8 · 10$^{-6g}$ | |

([a]Equilibrium binding constants (±standard deviation) obtained using FIDA unless otherwise noted. [b]Diffusion coefficient of the free analyte. [c]Diffusion coefficient of the complex. [d]Literature data (17). [e]Literature data (18). [f]Equilibrium binding constant obtained using ACE (±standard deviation). [g]Literature data (19))

The diffusion coefficients may be converted into hydrodynamic radii as previously described (3-7).

In order to further validate the procedure the equilibrium binding constant corresponding to the anion naproxenate with βCD was determined using standard Affinity Capillary Electrophoresis (ACE) under identical experimental conditions. The equilibrium binding constants obtained using the two methods are similar, albeit the results obtained using the ACE procedure appears slightly lower (table 1). This discrepancy is most likely due to Joule heating in electrophoresis which results in a higher temperature in the capillary.

In order to illustrate how the present invention may be used to estimate the concentration of an analyte preliminary experiments were performed on a simple model system composed of the ligand (affinity probe) α-naphthol and the analyte β-cyclodextrin (β-CD), which is frequently used as an additive in drug formulations. In FIG. 1 is shown the peak corresponding to 50 µM α-naphthol in the presence and absence of β-cyclodextrin, respectively.

Under the assumption of rapid on-and-off kinetics, the peak variances obtained from the raw data (FIG. 1) may be used to establish the binding isotherm in FIG. 2. The profile of the binding isotherm obtained using FIDA (FIG. 3) can both verify the binding stoichiometry and quantitatively determine the association constant, K. Each point in the binding isotherm (FIG. 2) is obtained using only a few nL injected sample.

Figure 3:
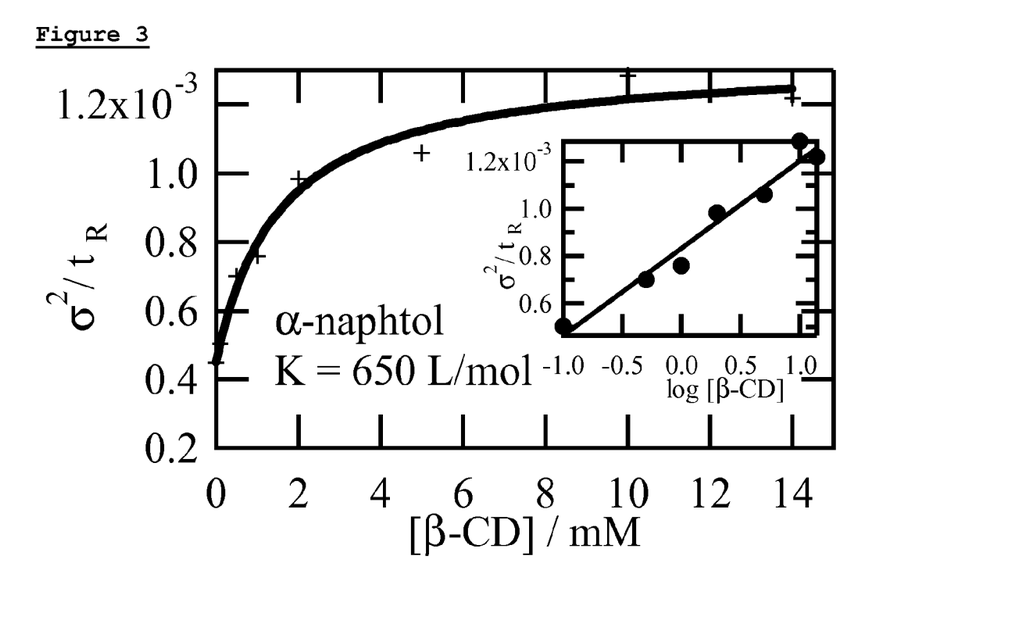
FIG. 3. Binding isotherm corresponding to the α-naphthol (ligand) β-CD (analyte) system based on peak variances, $\sigma^2$, divided by flow times, $t_R$. Inserted: linearised standard curve for determining concentrations FIG. 4. Linearized standard curve based on the data presented in FIG. 3. The figure displays peak variances, $\sigma^2$, divided by flow times, $t_R$ versus the base 10 logaritm of the β-CD concentration (the analyte). In this way an apparent linear relationship is obtained.
Figure 4:
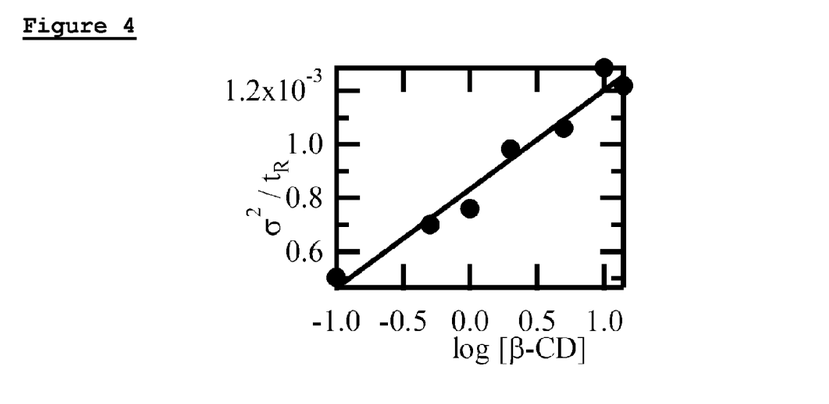

Inserted in FIG. 3 is a linearised standard curve (also presented in FIG. 4) linking a measured variance to a concentration of β-CD. The free β-CD concentration in unknown samples can thus be obtained from measurements of peak variances corresponding to added α-naphthol which functions as an analytical handle (ligand or affinity probe) for detection of β-CD; it is in this way that the present invention can be used for analyte quantification.

It can thus be concluded that FIDA is an effective and general way of obtaining equilibrium binding constants, diffusivities of both free analytes and complexes and estimating concentrations of an analyte in a sample. The advantages of the FIDA based procedure compared to existing methods include short analysis times, low sample volume requirements and simplicity of data analysis and instrumentation. In order to implement the methodology the only requirement is a fluid flow based analytical equipment such as HPLC, FIA or CE instrumentation, i.e. any suitable microfluidics system. Many of these commercially available instruments are equipped with autosamplers making high throughput analysis of non-covalent interactions and analyte quantification feasible. The present invention does not involve solid supports for immobilization or separation leading to a faster and cheaper analysis.

Finally, the methodology is relatively easy to couple to miniaturized chemical procedures including synthesis, sample preparation, and separation making direct analysis of non-covalent interactions of for example synthesized drugs and biological targets possible. Fully integrated procedures may be realized using microfluidic chip based systems. The procedure is easily coupled to other operations (including e.g. sample preparation and/or a chromatographic/electrophoretic separation) in a microfluidic system.

Relevant systems where the present invention is applicable would include antibody-antigen interactions (for quantification of antigens, the present method does not require separations or sandwich antibodies), complexes formed between DNA strands, DNA-RNA (for example for detection of single nucleotide polymorphisms, SNPs, infections, etc), complexes including PNA or LNA or similar synthetic nucleotides or detections of toxins in foodstuff, etc. In this way amino acids, polyamino acids, nucleotides, polynucleotides, saccharides, polysaccharides, antibodies, receptor proteins, signal proteins, enzymes, cofactors, cytokines, hormones, chemokines, polymers and drugs can be quantitated. Also the invention may be used to detect vira and bacteria using an antibody against the bacteria or by detection of whole DNA from a cell lysate employing an intercalating ligand.

FIDA on Differently Sized Ligands and Analytes

Flow Induced Dispersion Analysis (FIDA) can be applied to a number of different sizes of ligands and their corresponding analytes. Initial experiments revealed that the sensitivity of the assay depended on the size of the ligand and the corresponding analyte to be detected, which prompted the inventors to explore this issue. Surprisingly it is possible to improve the assay depending on the size of the ligand and the corresponding analyte to be detected.

The size of ligands and analytes can be divided into four categories

| Ligand | Analyte | Typical Ratio | Also described in: |
|---|---|---|---|
| Small | Small | 0.1-10 | Example 1 |
| Large | Large | 0.1-10 | Examples 2 and 3 |
| Small | Large | <0.1 | Example 5, 6 |
| Large | Small | >10 | Example 7 |

The ligand-to-analyte ratio is calculated as:

ratio=Mw(Ligand)/Mw(Analyte)

In the foregoing, and in general, the invention has been illustrated with reference to the interaction between two small molecules, such as α-naphthol or naproxen as ligands for the analyte β-cyclodextrin (βCD).

"Small/Small" Interactions

Small/Small interactions, such as the ones described above, and in example 1, can be analysed with the described FIDA assay. For the sake of clarity, Small molecules according to the invention are defined as having a molecular weight of less than 5 kDa, whereas large molecules are defined as having a molecular weight of above 5 kDa.

"Large/Large" Interactions

A large molecule (or particle) according to the present invention is defined as having a molecular weight above 5 kDa. The inventors have surprisingly realized that modifications to the protocol is needed when both the ligand and analyte are large molecules, as more time is required for the molecule to diffuse in the radial direction. This point may be realized on a qualitative level by the following relation between diffusion length (Δ), diffusion coefficient (D) and time (t):

$$\Delta = \sqrt{2Dt}$$

FIDA requires the dimensions of the flow channel or tube to be compatible with run time (that is peak appearance time which may be controlled be the pressure applied to pass the sample through the capillary), the diffusion coefficient of the ligand and the ligand-analyte complex (which is effectively related to size). Therefore conditions needs to be optimized depending on the absolute sizes of analyte and ligands as well as depending of the relative size of ligand compared to analyte.

Generally, when using FIDA to characterize the interactions between a ligand and an analyte the analyte should preferably be larger than the ligand (as in example 5) or similar size as in example 1 and 3, as this gives the best response.

"Small/Large" and "Large/Small" Interactions

A large effect on the apparent diffusivity is observed when a relatively large analyte binds to a comparably smaller ligand. On the other hand little effect will be observed when a small analyte binds to a comparably larger ligand (such as an antibody). In the latter case, adequate sensitivity may be obtained by introducing a competing binding equilibrium, where a fluorescently labeled small molecule analyte of known concentration binds to a large ligand (such as an antibody). In the presence of the large ligand the flow induced dispersion of the fluorescently marked analyte is observed to increase. When the mixture (fluorescently marked analyte and antibody against unknown concentration of unmarked analyte) is applied to a solution containing the unknown concentration of unmarked analyte (which is not fluorescently marked), the flow induced dispersion of the fluorescently marked analyte decreases as the unmarked analyte displaces the fluorescently marked analyte from the antibody. The change in observed dispersion correlates with the concentration of the unmarked analyte.

Unmarked analyte (UA)
Marked analyte (A)
Ligand (L)

By marked analyte is meant that it should be distinguishable from the corresponding unmarked analyte using the equipment for detection. The skilled person knows many ways to mark a molecule to make it distinguishable from others. One way is by fluorescently marking the molecule, but the marking may also be built into the molecule, such as isotope labeling/marking.

The below equation shows how y molecules of UA (Small molecule; concentration to be detected) inhibits competitively x molecules of the A-L complex (large molecule interacting with the marked analyte), thereby releasing A (small molecule; detectable marked analyte)

When the ratio of molecular weight of ligand-to-analyte is above 10 the difference in dispersion of the Large ligand vs. the Large ligand with the small Analyte bound is too small for quantitative applications when using the equipment as described in the present application.

The inventors have surprisingly found that the problem of measuring FIDA on Ligand-analyte systems with a Ligand-to-analyte ratio of above 10 may be solved by employing a coupled/competitive assay as described in example 7

Tuning of the Analyte Response/Response Curve

Using the FIDA assay it is possible to make a sigmodial dose response curve by assaying a range of different analyte concentrations. Such a sigmoidal response curve may be tuned to a higher or lower ED by modifying the concentration of the ligand as explained in the following.

The sigmoidal response curve of example 3 can be tuned to a higher or lower ED50 by modifying the concentration of the ligand—here BSA-FC. This point is rather important as it will significantly ease method development and optimisation of dynamic range. If a lower detection limit is required the concentration of the ligand is simply lowered which effectively displaces the response curve to lower values. The point is illustrated in the example involving fluorescent detection of BSA-FC. In the case of biomarkers, toxins and pathogens the relevant concentration range will vary considerably from case to case. In other methods based on for example ELISA substantial method development is required when going form one application to another. This is not the case with FIDA as the dynamic range is simply adjusted by selecting optimal ligand concentration.

The FIDA Assay

The present method include for quantification of an analyte by identification of a useful ligand or affinity probe in order to establish the necessary variation in dispersion/variance.

The method of measuring the concentration of an analyte in a sample according to the present invention includes the following steps:

selection of a ligand as the affinity probe for the analyte to be measured,
  establish in a flow based instrumentation, such as e.g. an agilent CE system, the variance for said ligand,
  establish the variance in the same instrumentation for the same concentration of said analyte in the presence of different (known) concentrations of the analyte to be measured in order to relate the concentration of analyte to the variance, establish the variance for the ligand in a sample, and
determine the concentration of the analyte in said sample by using the established relationship between the concentration of analyte and variance.

The variance may be established in different ways:
variance as obtained form a Gaussian fit to the peak (that is defined according to a Gaussian function),
variance obtained form the peak width (measured for example at half height),
Variance obtained as the second moment of the peak (i.e. from an analysis of the statistical moments corresponding to the peak),
or similar related procedures.

In one specific embodiment of the invention, a Gaussian fit is used in the method:

The concentration of an analyte in a sample is measured by including the following steps:
selection of a ligand as an affinity probe for the analyte to be measured,
establish in a flow based instrumentation, such as e.g. an Agilent CE system, the variance ($\sigma^2$) for said ligand, obtained from a Gaussian fit to the peak corresponding to the ligand,
step 2 is repeated with different concentrations of the analyte in the flowing solution,
$\sigma^2$ or $\sigma^2/tr$ is plotted against analyte concentration (standard curve is established),
establish the variance ($\sigma^2$) for the ligand in a sample, and
determine the concentration of the analyte in said sample by using the plot (standard curve) from step 4.

Alternative experimental procedures for measuring the variance/flow induced dispersion (step 2):
A sample containing the ligand (or affinity probe) and the analyte is injected into a flowing stream of liquid containing the analyte and the flow induced dispersion of the ligand is measured
A sample containing the ligand and the analyte is injected into a sample zone of the analyte and the flow induced dispersion of the ligand is measured
A sample containing the ligand and the analyte is injected into a flowing stream of liquid and the flow induced dispersion of the ligand is measured.

The relationship between variance observed for the ligand and the analyte be determined in many ways. For instance the ligand concentration can be kept at a constant concentration, and the concentration of analyte varied. In this way a standard curve where the only parameter varied (analyte) can be obtained.

A standard curve may be obtained from in different ways:
a—The variance vs analyte concentration
b—Variance/tr vs analyte concentration
c—Tr/variance vs analyte concentration
d—Apparent diffusion coefficient vs analyte concentration
Example a-d on a logarithmic scale.

The present invention relates to a method for measuring the concentration of an analyte in a sample comprising the following steps:
1) selecting a ligand as an affinity probe for the analyte to be measured,
2) determine in a flow based instrumentation the variance for said ligand,
3) determine the variance in the same instrumentation for the same concentration of said ligand in the presence of different (known) concentrations of the analyte,
4) relate the concentrations of analyte to the variances determined in step c,
5) adding a known amount of ligand to a sample comprising an unknown concentration of analyte,
6) determine the variance for the ligand in the sample introduced/added in step e, and
7) determine the concentration of the analyte in said sample by using the relationship established in step d and the variance determined in step f.

The invention further relates to a method comprising
1) selecting a ligand as an affinity probe for the analyte to be measured,
2) determine in a flow based instrumentation, such as e.g. an agilent CE system, the variance ($\sigma^2$) for said ligand, obtained from a Gaussian fit to the peak corresponding to the ligand,
3) repeating step b with said ligand and different known concentrations of the analyte,
4) plotting $\sigma^2$ or $\sigma^2/tr$ against the analyte concentration,
5) determine the variance ($\sigma^2$) for the ligand in a sample comprising the analyte, and
6) determine the concentration of the analyte in said sample by using the plot from step d.

The present invention also relates to kits for performing the method as discussed above in full or in part.

The invention further relates to methods and kit for measuring the concentration of more than one analyte, such as 2, 3, 4, 5, 6, 7, 8, 9, 10 or even more than 10 different analytes.

Supplementary FIDA Applications

The following lists of applications is likely to be realisable using FIDA. It is supplementary to the application involving BSA/antiBSA or DNA.

1) In a related application a sandwich immunoassay is realized using FIDA. In this example the flow induced dispersion of a fluorescently marked antibody is detected in the presence of an antigen and a primary antibody.

2) In a related application a DNA, RNA or LNA strand is detected by measuring the flow induced dispersion of a labeled complementary strand. This application may involve detection/characterization of single nucleotide polymorphisms (SNPs).

3) In a related application a virus is detected (such as e.g. H1N1) by detecting the flow induced dispersion of an antibody against the virus.

4) In a related application a bacteria is detected, by detecting the flow induced dispersion of an antibody against the bacteria.

5) In a related application a toxin (present in a biological sample, foodstuff, or water samples) is detected, by detecting the flow induced dispersion of a chemical entity interacting with the toxin.

6) In related applications aptamers are used in place of traditional antibodies.

7) In a related application flow induced dispersion is used in combination with competitive binding for analyte quantification.

8) In a related application, standard addition of a marker compound used for FIDA is employed for analyte detection/quantification.

9) In a related application FIDA is used to quantify DNA using an intercalating dye. The DNA sample may be a cell lysate obtained from dairy products (milk samples), fermentation processes, etc. FIDA may be used in combination with other flow based equipment for cell analysis such as eg flow cytometry (FCM). FIDA is suited for the analysis of raw milk (unpasteurized milk) to detect possible pathogens such as for example E. Coli O157:H7, Listeria, and Salmonella The listed applications may involve different levels of quantification.

Example 1

(refering to the illustrative example and figures discussed above. Below is given the detailed experimental procedures for obtaining the standard curves in FIGS. 3 and 4)

Reagents.

βCD, α-naphthol and naproxen was obtained form Sigma-Aldrich. Sodium dihydrogenphosphate monohydrate was obtained from Merck (Darmstadt, Germany). All chemicals were used as received. The amount of water present in βCD was determined by gravimetric analysis upon drying to constant weight in vacuo at ~60° C. Purified water from a Milli-Q deionization unit (Millipore, Bedford, Mass., USA) was used throughout. The sample and running buffer was a 67 mM sodium phosphate buffer, pH 7.40, prepared from sodium dihydrogenphosphate monohydrate; this buffer was used for all analytes. The pH was adjusted by addition of 5 M NaOH. The sample and run buffer contained varying amounts of βCD. Stock solutions of α-naphthol and naproxen ($1.0 \cdot 10^{-3}$ M) were prepared in 10% (v/v) acetonitrile/phosphate buffer. Samples were prepare by appropriate dilution using the βCD 67 mM phosphate run buffer solutions.

Instrumentation.

Flow induced dispersion and capillary electrophoresis experiments were carried out using an Agilent $^{3D}$CE instrument (Agilent Technologies, Waldbronn, Germany). Uncoated fused silica capillaries of 48.5 cm total length (50 μm i.d., 360 μm o.d.) and 40.5 cm to the detection window were obtained from Polymicro Technologies (Phoenix, Ariz., USA).

CE and FIDA Procedures.

New capillaries were conditioned with 1 M NaOH (45 min), Milli-Q water (30 min) and 67 mM phosphate buffer pH 7.4 (30 min). Before a series of experiments the capillary was refreshed by flushing with 1 M NaOH (10 min) and 67 mM phosphate buffer pH 7.4 (10 min). In FIDA, the capillary was preconditioned by flushing the capillary with 0.1 M NaOH (2 min) and run buffer (2 min). The sample was injected by applying a pressure of 50 mbar for 5 sec. Subsequently a pressure of 50 mbar was applied across the capillary to force the sample through it. Finally the sample was detected by UV absorbance at 230 nm. Samples were run in triplicate. The peak variance was obtained by fitting the UV signal to a Gaussian peak shape. The Gaussian in addition to peak variance and peak appearance time the function incorporates a constant A to account for signal height and a constant y0 to account for a possible detector offset.

Example 2

Flow induced dispersion analysis (FIDA) may be used for diagnostic purposes and for quantifying biomarkers. The following example involves an antibody (anti-BSA) and an antigen (BSA-FC). The conditions are as in example 1 with the following modifications.

The dispersion of BSA-FC (Bovine serum albumin marked with a fluorophore (flourescein isothiocyanate), SIGMA A9771)) is measure in a fused silica capillary (50 micrometer inner diameter) using UV detection at 500 nm (495 nm). Injection hydrodynamic injection was employed (50 mbar, 5 seconds). The following procedure was used for freshly conditioned fused silica capillaries (example 1). The capillary was flushed (1 bar) 2 minutes with 0.1 M NaOH, 1 minute using phosphate buffer (67 mM pH 7.4) 2 minutes using phosphate buffer (67 mM pH 7.4) and 5 minutes using the run buffer (phosphate buffer containing the analyte, antiBSA). The temperature was maintained at 25° C.

Other conditioning procedures and detection wavelengths may be used and other detectors may be used such as e.g. detection based on fluorescence, electrochemistry, potentiometry or in certain cases mass spectrometry. Other miniaturised flow systems may be used.

A sample of $10^{-5}$ M BSA-FC is injected hydrodynamically into a flowing stream of 67 mM phosphate buffer pH 7.4. By pressure the injected sample is pushed through the fused silica capillary and detected by uv-vis absorbance detection at 500 nm (495 nm). Due to the parabolic flow profile the sample of BSA-FC is subject to dispersion as observed by the Gaussian peak shape. The dispersion is related to the apparent diffusion coefficient of BSA-FC.

The apparent (i.e. observed) diffusivity of BSA-FC will change when it is engaged in a non-covalent binding equilibrium with for example an antibody such as Anti-BSA (SIGMA B2901). When the anti-bsa is introduced in the fused silica flow channel in the dispersion zone, the binding is reflected in a dispersion change.

By conducting the experiments it will be possible to quantitative characterize the BSA-FC-Anti BSA binding event by using appropriate binding curves. The data evaluation will based on Gaussian fits the dispersed signal corresponding to BSA-FC. The exact data analysis will depend on whether the binding kinetics is fast compared to the timescale of the experiment, slow compared to the timescale of the experiment or if an intermediate binding kinetics is in play on the timescale of the experiment.

Alternative experimental methods and data analysis: Instead of pressure driven flow an electroosmotic flow may be employed.

In a related application quantitative knowledge of the non-covalent interaction (i.e. the association or dissociation constant obtained by FIDA) may be used to determine the unknown concentration of anti-bsa based on measuring the dispersion pertaining to BSA-FC injected into a dispersion zone of anti-bsa.

In a related application the sample containing anti-bsa may be a buffer solution, urin sample or a blood sample or another biofluid.

In a related application the concentration of anti-bsa is determined form a "system standard curve". The "system standard curve" is obtained from measuring the dispersion of BSA-FC in a liquid containing known concentrations of anti-BSA. The unknown concentration of BSA in the same liquid can thereafter be determined from a simple dispersion measurement of bsa-fc in the liquid.

The application described above may be realized in an integrated microfluidic system.

Example 3

FIDA may be used to characterise the interactions between a large molecule as ligand (Anti-BSA) and a large molecule as analyte (BSA-FC), as illustrated in this example.

The dispersion of BSA-FC (Bovine serum albumin marked with a fluorophore (flourescein isothiocyanate), SIGMA A9771)) is measure in a fused silica capillary (50 micrometer inner diameter) using UV detection at 495 nm. Injection hydrodynamic injection was employed (50 mbar, 5 seconds). The following procedure was used for freshly conditioned fused silica capillaries (example 1). The capillary was flushed (1 bar) 2 minutes with 0.1 M NaOH, 1 minute using phosphate buffer (67 mM pH 7.4) 2 minutes using phosphate buffer (67 mM pH 7.4) and 5 minutes using the run buffer (phosphate buffer containing the analyte, antiBSA). The concentration of BSA-FC was 10 μM.

The detected UV signal gives rise to a Gaussian peak shape from which the peak variance may be obtained as described in example 1 by fitting the detector response to a Gaussian peak shape.

Figure 5:
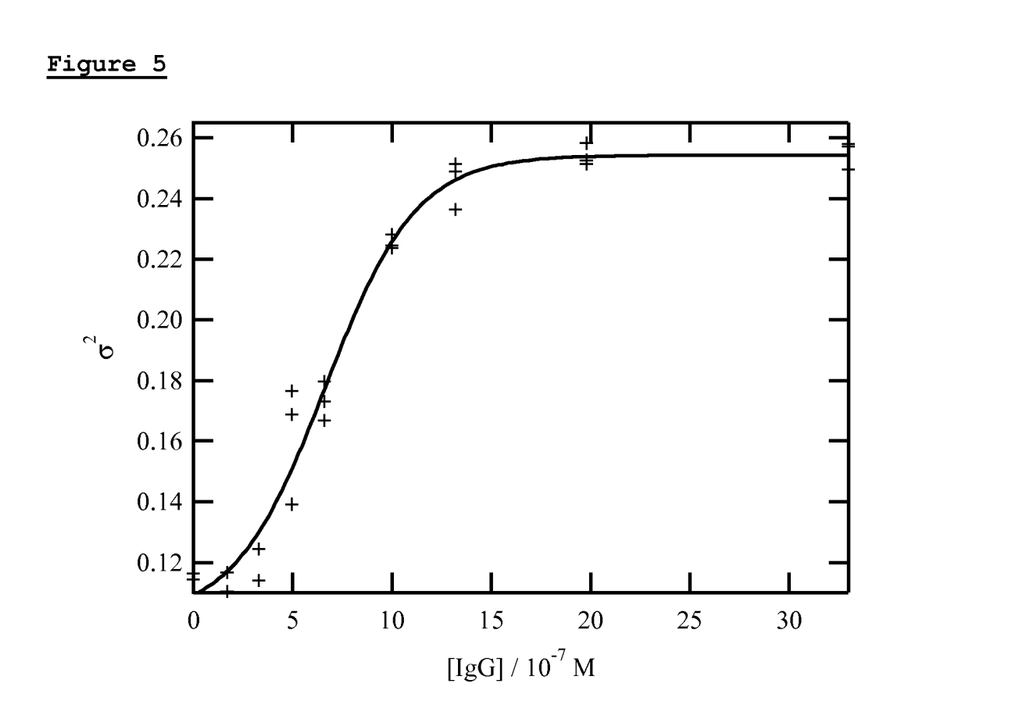

In FIG. 5 is observed the peak variance obtained from gaussian fits to the peak shapes at different concentrations of anti-BSA. This gives rise to a sigmoidal standard curve having an inflection point close to 7 μM anti-BSA.

Figure 6:
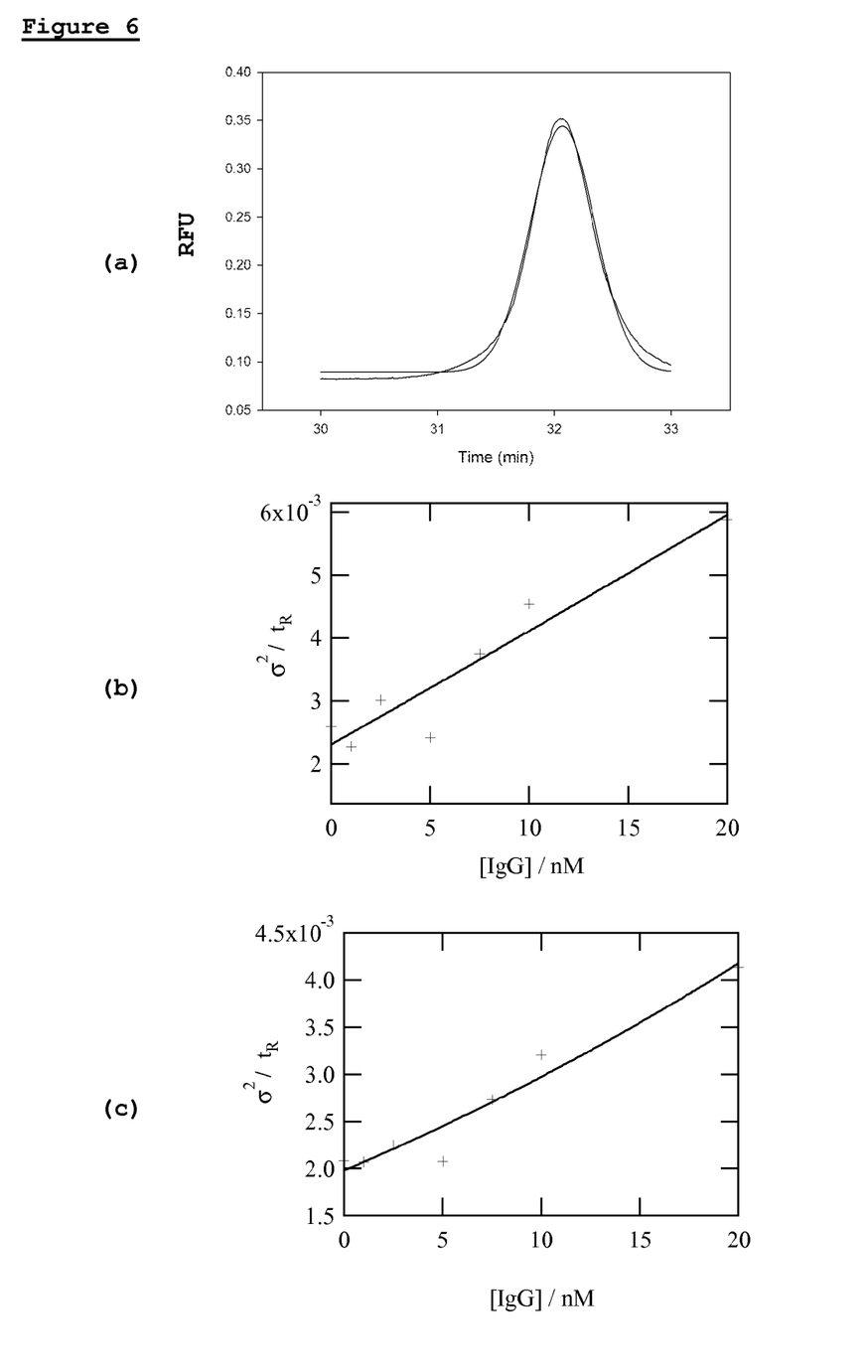
FIG. 6. Is a further figure based on the data obtained in example 3. (a) illustrates a Gaussian fit to the peak corresponding to BSA-FC (employing fluorescent detection of the fluorescein isothiocyanate tag) in the absence of anti-BSA. (b) illustrates the peak variance determined from a Gaussian fit to the peak corresponding to BSA-FC in the presence of different amounts of anti-BSA (IgG) and (c) is a gaussian fit of the data also presented in b but using a modified Gaussian fit.

In FIG. 6 is shown a similar experiment but employing flourescent detection as shown in FIG. 6. The fluorescent detector was the evolution model equipped with 488 nm LIF detection obtained form picometrics.

Figure 7:
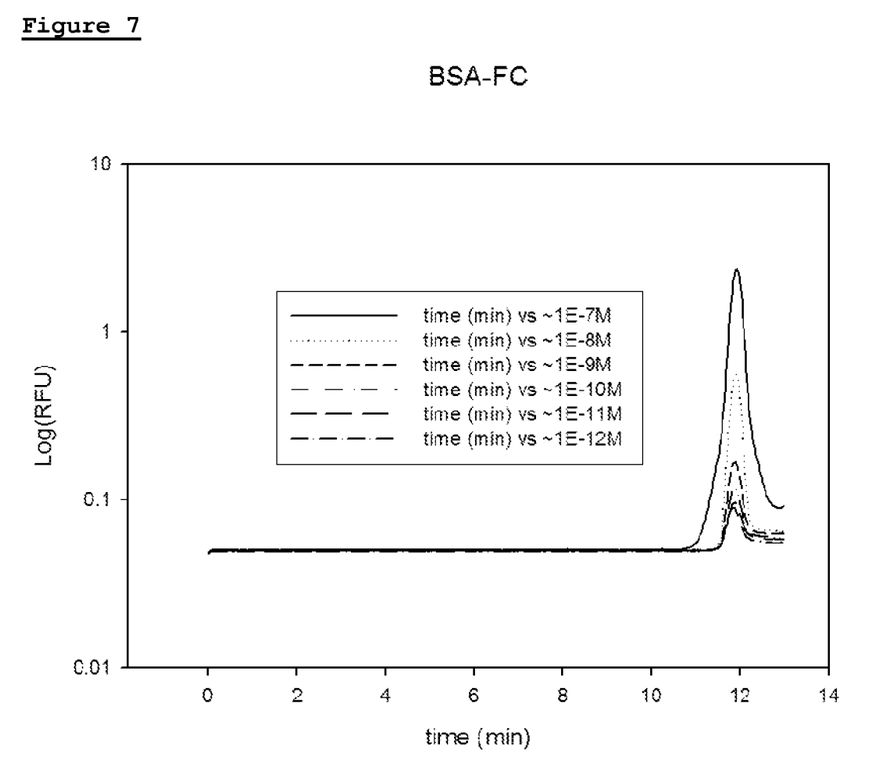
FIG. 7. Detection limits in the picomolar range (laser induced fluorescent (LIF) detection at 488 nm excitation) of the ligand BSA-FC based on the system of detecting anti-BSA analyte using BSA-FC ligand, which is described in example 4.

In this case the concentration of BSA-FC was 1 nM which allowed the standard curve to be shifted to the nM-range (FIG. 6b). As shown in FIG. 7 it may in principle be possible to shift the standard curve to even lower concentrations as a clearly detectable peak was obtained even at 1 μM BSA-FC (corresponding to about 6000 molecules BSA-FC).

Example 4

FIDA may be used in the pico molar range, as justified by the following example. FIG. 7 displays experiments with BSA-FC, demonstrating that BSA-FC may be detected even at pM concentrations. It is therefore justified that the standard curves in FIGS. 5 and 6 may even be further shifted to lower concentrations.

As evident from the above example, the FIDA method is likely to be applicable to a low concentration of 1 picomolar, representing just 6000 molecules under the present conditions.

Example 5

Figure 8:
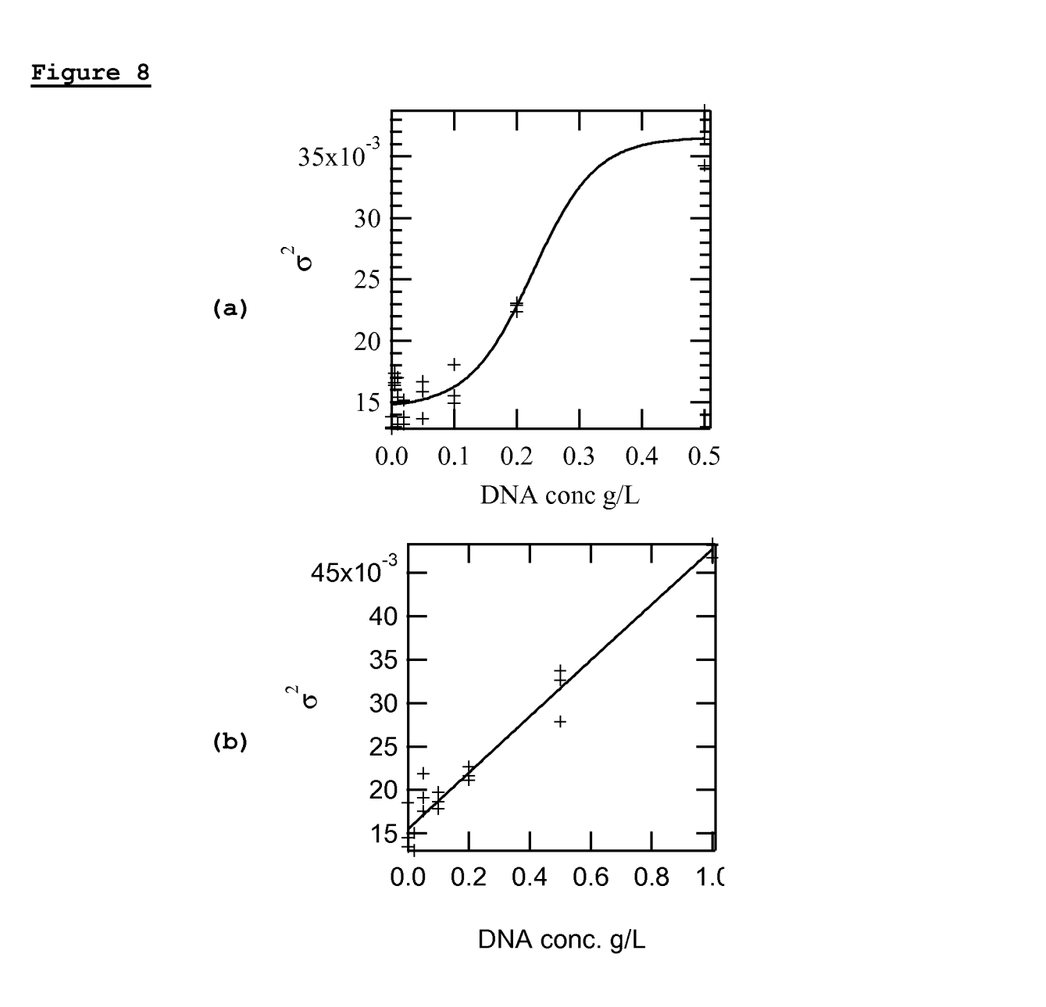
FIG. 8. Total DNA detection, as illustrated in example 5. (a) High molecular weight DNA (Deoxyribonucleic acid sodium salt from salmon testes, sigma D1626 using an intercalating dye as ligand (berberine chloride, sigma B3251); (b) Low molecular weight DNA (deoxyribonucleic acid, low molecular weight from salmon sperm, sigma 31149).

FIDA may be used to monitor biological activity based on e.g. detecting DNA fragments from bacteria. In this example the interactions between a small molecule as ligand (berberine chloride, sigma B3251) and a large molecule as analyte (DNA) is illustrated in FIG. 8. The conditions where as in example 3 except that UV detection was performed at 345 nm. As evident from FIG. 8 the detection of low as well as high molecular weight dna fragments may be realized using FIDA employing an intercalating or interacting dye as ligand for DNA.

Detection of DNA fragments from bacteria has numerous applications. For instance, the quality of milk may be immediately inspected on-site at the farm by the farmer prior to pooling the milk together with other milk in the tank of the truck picking up milk from farmers. Detecting DNA fragments from bacteria on-site using FIDA represents a significant advantage, as contaminated or sub-standard milk can be detected at the farm, in the earliest possible place in the value chain of milk refining.

In general detection of whole DNA is applicable in any industrial or research setting where vira or bacteria needs to be quantified. Additional examples include (but is not limited to): somatic cells, sperm cells, mammalian cells, animal cells, yeast cells etc. Being a flow based method FIDA may be coupled to flow cytometry (FCM).

Example 6

FIDA may be used to characterise the interactions between a small molecule as ligand (bromcresol green) and a large molecule as analyte (HSA), as illustrated in this example.

Figure 9:
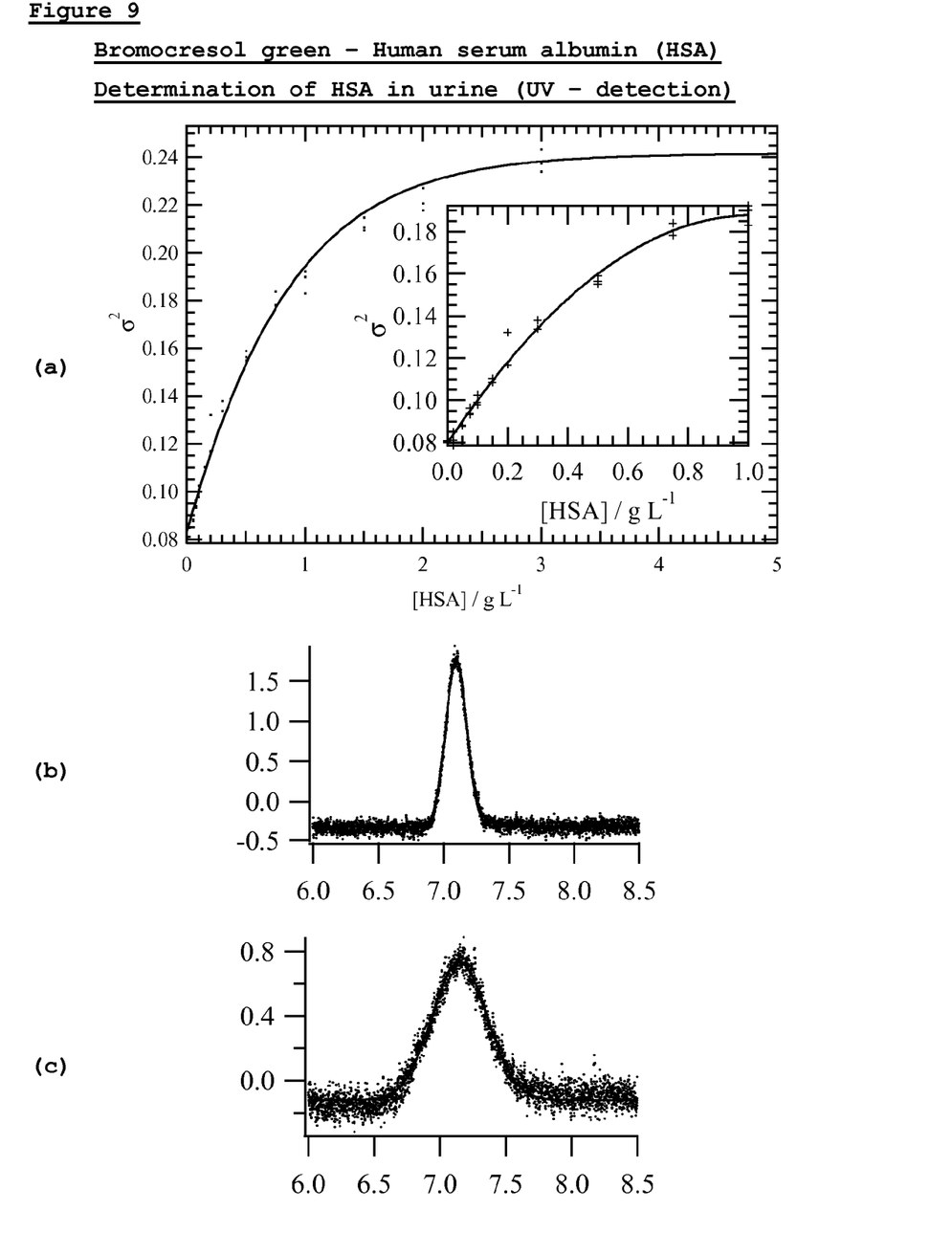
FIG. 9. FIDA used to detect markers of biological fluid (Human Serum Albumin (HSA, Fluka 05418)), in urine), as illustrated in example 6 employing bromocresole green (sodium salt, Sigma 17480) as ligand. (a) Peak variances corresponding to bromocresole green in the presence different amounts of HSA (insert: close-up at low HSA concentrations; (b) Peak corresponding to 50 μM bromocresole green employing uv detection at 595 nm; (c) As (b) but in the presence of 1.5 g/L HSA.
Figure 10:
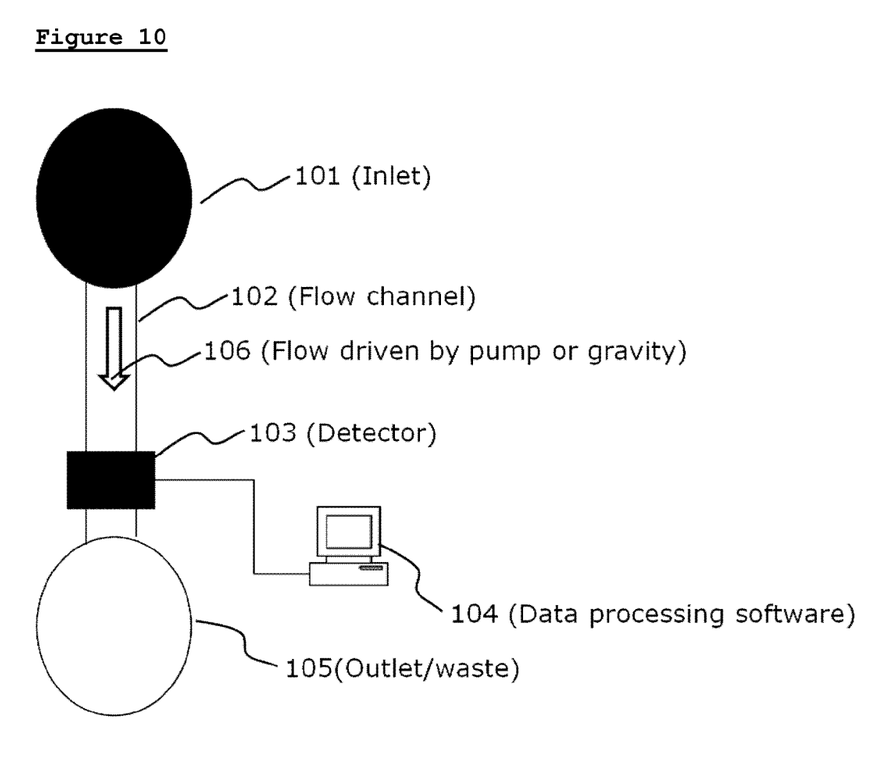
FIG. 10. Outline of a device for conducting FIDA comprising an inlet (101) where ligand and analyte is introduced; flow channel (102); detector (103); coupled to data processing unit (104); outlet/waste (105). The flow may be driven by gravity, a pump or by an electroosmotic flow (106).

The conditions pertaining to FIG. 9 is similar to those described in example 3 except that uv detection was performed at 595 nm, and that the run buffer was artificial urine (composed of NaCl, KCl, sodium phosphate buffer, and creatinine).

As evident from example 6, FIDA may be used to detect markers from biological fluid, such as blood, urine, saliva, sweat, cerebrospinal fluid.

FIDA is well suited for the case where the ligand is smaller than the analyte as a large effect on the peak dispersion is observed when the ligand is bound to the analyte. The applications are not limited to biological fluids, but may be applied in other areas such as agriculture, quality control of e.g. fermentation processes or fast on site detection of pathogens.

Example 7

FIDA may be used to characterise the interactions between a large molecule as ligand (mono or polyclonal antibodies against one or more aflatoxins) and a small molecule as analyte (aflatoxins), as illustrated in this example.

The present example employs two ligands: a fluorescently marked aflatoxin and an antibody against aflatoxin. The analyte is aflatoxin. In a first series of experiments the binding between fluorescently marked aflatoxin and an antibody against aflatoxin is examined by FIDA. This procedure is similar to example 6. The conditions where the antibody binds a significant amount of fluorescently marked aflatoxin (ideally all) is established. In a second set of experiments a fixed concentration of fluorescently marked toxin and antibody against aflatoxin is employed and different concentrations of aflatoxins are used. At comparatively high concentrations of aflatoxin, the aflatoxin displaces fluorescently marked aflatoxin from the antibody complex giving rise to an apparent lower peak variance. In this case the standard curve for concentration determinations will thus feature an apparent high peak variance at low concentrations of aflatoxin and an apparent small peak variance at high concentrations of aflatoxin.

Prior to each experiment the capillary inlet is carefully rinsed. Also new, freshly conditioned capillaries may advantageously be used The experimental conditions are otherwise as described in example 3 and 6.

In the above example, the ligand may also comprise of a plurality of ligands, such as a mixture of monoclonal antibodies against each of the four aflatoxins. This would allow a detection of the presence of aflatoxins in e.g. grains on-site at the farm. The simple and easily conducted procedure would allow for the food producers to routinely and cheaply screen all batches of grain, as opposed to random spot checks. This would increase the overall food safety. Toxins such as aflatoxins, zearalenone, Deoxynivalenol (DON), ochratoxin would be suitable to test according to the present method.

In addition to being a competitive assay one should also realize that the binding ligands fulfils the rule that it should be small compared the first ligand (which could be a polyclonal or monoclonal antibody in the present example).

Example 8

The data are fitted using a 4 parameter Gaussian function allowing to take into account possible detector offset. Additional details concerning fitting procedures may be found in reference 20.

REFERENCES

1. Drews, J. *Science* 2000, 287, 1960-1964.
2. Weigl, B. H.; Bardell, R. L.; Cabrera, C. R. *Adv. Drug Deliver. Rev.* 2003, 55, 349-377.
3. Bello, M. S.; Rezzonico, R.; Righetti, P. G. *Science* 1994, 266, 773-776.
4. Cottet, H.; Martin, M.; Papillaud, A.; Souaid, E.; Collet, H.; Commeyras, A. *Biomacromolecules* 2007, 8, 3235-3243.
5. Le Saux, T.; Cottet, H. *Anal. Chem.* 2008, 80, 1829-1832.
6. d'Orlye, F.; Varenne, A.; Gareil, P. *J. Chromatogr. A* 2008, 1204, 226-232.
7. Ostergaard, J.; Jensen, H. *Anal. Chem.* 2009, 81, 8644-8648.
8. Sharma, U.; Gleason, N. J.; Carbeck, J. D. *Anal. Chem.* 2005, 77, 806-813.
9. Burkey, T. J.; Griller, D.; Lindsay, D. A.; Scaiano, J. C. *J. Am. Chem. Soc.* 1984, 106, 1983-1985.
10. Montanari, M. L. C.; Montanari, C. A.; Veloso, D. P.; Beezer, A. E.; Mitchell, J. C.; Volpe, P. L. O. *Quant. Struct.-Act. Rel.* 1998, 17, 102-108.
11. Clark, S. M.; Konermann, L. *J. Am. Soc. Mass Spectr.* 2003, 14, 430-441.
12. Cottet, H.; Biron, J. P.; Martin, M. *Anal. Chem.* 2007, 79, 9066-9073.
13. Taylor, G. *Proc. R. Soc. Lon. Ser.-A* 1953, 219, 186-203.
14. Aris, R. *Proc. R. Soc. Lon. Ser.-A* 1956, 235, 67-77.
15. Taylor, G. *Proc. R. Soc. Lon. Ser.-A* 1954, 225, 473-477.
16. Lucas, L. H.; Price, K. E.; Larive, C. K. *J. Am. Chem. Soc.* 2004, 126, 14258-14266.
17. Rekharsky, M. V.; Inoue, Y. *Chem. Rev.* 1998, 98, 1875-1917.
18. Bourne, J. R.; Tovstiga, G. *Chem. Eng. Commun.* 1985, 36, 67-71.
19. Zhang, H. X.; Annunziata, O. *Langmuir* 2009, 25, 3425-3434.
20. Jensen, H.; Oestergaard, J. *J. Am. Chem. Soc.*, 2010, 132, 4070-4071

The invention claimed is:

1. A method for measuring the concentration of an analyte in a sample, comprising:
   (a) for each of a plurality of concentrations of the analyte:
      (i) flowing the analyte in the presence of a concentration of a ligand, in solution under pressure through a narrow tube, capillary, or channel, wherein the ligand is an affinity probe of the analyte and forms a complex with the analyte, wherein the flowing satisfies conditions of Taylor dispersion, and wherein at least one of the plurality of concentrations of the analyte is zero;
      (ii) measuring the flow induced dispersion of the ligand by detecting a UV or fluorescence signal generated by the ligand; and
      (iii) calculating a variance of a peak of the signal;
   (b) generating a curve of the peak variances from step (a) by plotting the peak variances against their respective analyte concentrations, thereby generating a standard curve;
   (c) flowing the analyte from the sample in the presence of the concentration of the ligand under pressure through the narrow tube, capillary, or channel, wherein the flowing satisfies conditions of Taylor dispersion;
   (d) measuring the flow induced dispersion of the ligand by detecting a UV or fluorescence signal generated by the ligand of step (c) with the detector;
   (e) calculating a variance of a peak of the signal from step (d); and
   (f) comparing the variance from step (e) to the standard curve,
   wherein the closest match between the variance from step (e) and a point on the standard curve determines the concentration of the analyte in the sample.

2. The method of claim 1, wherein the variances are calculated as $\sigma^2$ of the peak signal, obtained from a Gaussian fit to the peak, and wherein the generating of the curve in step (b) of the peak variances from step (a) comprises plotting $\sigma^2$, or $\sigma^2$ divided by a flow time of the ligand, for each analyte concentration.

3. The method of claim 1, wherein the ligand and analyte are both large.

4. The method of claim 1, wherein a capillary electrophoresis system, a high performance liquid chromatography system, a flow cytometry system, or a flow injection analysis system comprises the narrow tube, capillary, or channel.

5. The method of claim 1, wherein the ligand comprises a detectable label.

6. The method of claim 1, wherein the sample is a bodily fluid.

7. The method of claim 1, wherein the sample is a food sample.

8. The method of claim 7, wherein the food sample is a dairy product.

9. The method of claim 7, wherein the food sample does not comprise a dairy product.

10. A method for measuring the concentration of a first analyte in a sample, comprising:
   (a) for each of a plurality of concentrations of the first analyte:
      (i) flowing the first analyte in the presence of a concentration of a ligand and a concentration of a second analyte, in solution under pressure through a narrow tube, capillary, or channel, wherein the ligand is an affinity probe of the first analyte and the second analyte and forms a complex with the first analyte and alternatively forms a complex with the second analyte, wherein the second analyte is distinguishable from the second analyte, and wherein the flowing satisfies conditions of Taylor dispersion;
      (ii) measuring the flow induced dispersion of the second analyte by detecting a UV or fluorescence signal generated by the second analyte; and
      (iii) calculating a variance of a peak of the signal;
   (b) generating a curve of the peak variances from step (a) by plotting the peak variances against their respective first analyte concentrations, thereby generating a standard curve;
   (c) flowing the first analyte from the sample in the presence of the concentration of the ligand and of the concentration of the second analyte under pressure through the narrow tube, capillary, or channel, wherein the flowing satisfies conditions of Taylor dispersion;
   (d) measuring the flow induced dispersion of the second analyte by detecting a UV or fluorescence signal generated by the second analyte of step (c) with the detector;
   (e) calculating a variance of a peak of the signal from step (d); and
   (f) comparing the variance from step (e) to the standard curve,
   wherein the closest match between the variance from step (e) and a point on the standard curve determines the concentration of the first analyte in the sample.

11. The method of claim 10, wherein the variance is calculated as $\sigma^2$ of the peak signal, obtained from a Gaussian fit to the peak, and wherein generating of the curve in step (b) of the peak variances from step (a) comprises plotting $\sigma^2$, or $\sigma^2$ divided by a flow time of the second analyte, for each first analyte concentration.

12. The method of claim 10, wherein the ligand is large and the first analyte is small.

13. The method of claim 10, wherein a capillary electrophoresis system, a high performance liquid chromatography system, a flow cytometry system, or a flow injection analysis system comprises the narrow tube, capillary, or channel.

14. The method of claim 10, wherein the ligand comprises a detectable label.

15. The method of claim 10, wherein the sample is a bodily fluid.

16. The method of claim 10, wherein the sample is a food sample.

17. The method of claim 16, wherein the food sample is a dairy product.

18. The method of claim 16, wherein the food sample does not comprise a dairy product.

\* \* \* \* \*